United States Patent
Sekine et al.

(10) Patent No.: US 7,569,685 B2
(45) Date of Patent: Aug. 4, 2009

(54) ARTIFICIAL RNAÓS MODIFIED AT THE 2Ó-HYDROXYL GROUP

(75) Inventors: Mitsuo Sekine, Yokohama (JP); Kohji Seio, Yokohama (JP); Hisao Saneyoshi, Yokohama (JP)

(73) Assignee: Japan Sciencce and Technology Agency, Kawaguchi-shi (JP)

( * ) Notice: Subject to any disclaimer, the term of this patent is extended or adjusted under 35 U.S.C. 154(b) by 258 days.

(21) Appl. No.: 10/591,291

(22) PCT Filed: Mar. 2, 2005

(86) PCT No.: PCT/JP2005/003459

§ 371 (c)(1),
(2), (4) Date: May 10, 2007

(87) PCT Pub. No.: WO2005/085271

PCT Pub. Date: Sep. 15, 2005

(65) Prior Publication Data

US 2008/0021206 A1 Jan. 24, 2008

(30) Foreign Application Priority Data

Mar. 4, 2004 (JP) .............................. 2004-060261

(51) Int. Cl.
*C07H 21/00* (2006.01)
(52) U.S. Cl. ..................... 536/25.3; 536/22.1; 536/23.1
(58) Field of Classification Search ........................ None
See application file for complete search history.

(56) References Cited

FOREIGN PATENT DOCUMENTS

WO  WO-02/20546 A1  3/2002

OTHER PUBLICATIONS

Pierre Martin; Ein neuer Zugang zu 2'-O--Alkylribonucleosiden und Eigenschaften deren Oligonucleotide, Helvetica Chimica Acta., vol. 78, pp. 486-504, 1995.
Morten Grotli et al., 2 -O-(Carbamoylmethyl) oligoribonucleotides., Terahedron, 55, 1999, pp. 4299-4314.
M.G.J. Beets et al., Macrocyclic oxalactones, Rev.trav.chim., 1953, vol. 72, pp. 411-418.

*Primary Examiner*—Patrick T Lewis
(74) *Attorney, Agent, or Firm*—Birch Stewart Kolasch & Birch LLP

(57) ABSTRACT

The purpose of the present invention is to develop a system for efficiently constituting cyanoethyl ethers under mild conditions and probability of the ethers as functional groups for imparting specific functions and to make a contribution to the production of novel functional nucleic acids.

The present invention relates to a nucleoside that is represented by the general formula (I) or a nucleotide derived therefrom:

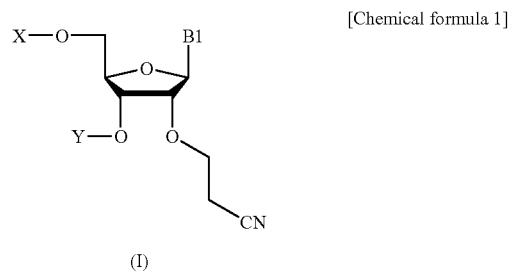

(I)

wherein X and Y may be the same as or different from each other, and are hydrogen, optionally substituted silyl group, 4-methoxytrityl group, 4,4'-dimethoxytrityl group or a group represented by the general formula (II):

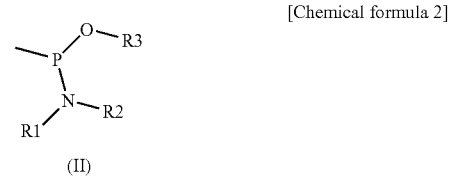

(II)

wherein R1 and R2 may be the same as or different from each other, representing an alkyl group having 1-7 carbon atoms such as diisopropyl, or they are united with each other to form a ring structure, R3 represents a protective group for a phosphoric acid such as 2-cyanoethyl; and B1 represents an optionally substituted pyrimidine or purine base.

16 Claims, 1 Drawing Sheet

ARTIFICIAL RNAÓS MODIFIED AT THE 2Ó-HYDROXYL GROUP

TECHNICAL FIELD

The present invention relates to a nucleoside, a nucleotide and their phosphoramidite compound, which have a cyanoethyl ether group at 2' hydroxyl group. These compounds may be used as a chemical agent for the synthesis of a nucleic acid or as modified RNA.

BACKGROUND ART

A chemically synthesized oligoribonucleotide (oligo RNA) may be used as a RNA probe for gene analysis; materials for RNA pharmaceuticals such as antisense RNA, ribozyme RNA, and gene interference by means of iRNA; artificial enzymes, and an adaptor.

A RNA derivative having a methyl ether group at its 2' hydroxyl group is commercially available and widely used as that of an ether-type. However, this modified RNA has a disadvantage with respect to enzyme-resistance in cells when it is used as a gene-controlling agent. Another ether-type modified RNA widely used is one having a methoxyethylether group. This modified RNA was reported to be superior in the enzyme-resistance to that having the methyl group (Non-Patent Document 1). However, there is no common way for the synthesis of the methoxyethylether-type modified RNA with the use of pyrimidine and purine nucleosides due to limitations in a method and agent for the introduction of said group. Furthermore, as the structure of its ether chain is restricted due to an oxygen atom present therein, it is very likely that a problem will occur with respect to condensation efficiency in the synthesis of the oligo RNA.

In order to overcome the above problems, it is necessary to develop an ether-type modified RNA with a group of around three carbon atoms that has a hydrophilic and electron-accepting substituent at its end but no oxygen atom in the ether chain.

Non-Patent Document 1: Von Pierre Martin, Helvetica Chimica Acta 1995, 78, 486-504

SUMMARY OF THE INVENTION

Problems to be Solved by the Invention

One potential ether-type modified RNA that will satisfy the above conditions may be that of a cyanoethylether-type. This modified RNA has an advantage that it can be economically obtained with the use of acrylonitrile as its introducing agent. However, it has a disadvantage as well that the introduction of the above ether will need severe conditions of heating with a strong base such as sodium hydroxide. And, utility of the cyanoethylether group as a functional moiety has not yet been developed.

The purpose of the present invention is to develop a system for efficiently constituting cyanoethyl ethers under mild conditions and probability of the ethers as functional groups for imparting specific functions and to make a contribution to the production of novel functional nucleic acids.

Means for Solving the Problems

The present inventors have searched a base that is most suitable for activating a 2' hydroxyl group while acrylonitrile is used as a material for 2-cyanoethylation, and have completed the present invention.

The present invention thus relates to a nucleoside represented by the general formula (I) and nucleotide derived therefrom, in which X and Y may be the same as or different from each other, and are hydrogen, optionally substituted silyl group, 4-methoxytrityl group, 4,4'-dimethoxytrityl group or a group represented by the general formula (II) wherein R1 and R2 may be the same as or different from each other, representing an alkyl group having 1-7 carbon atoms such as diisopropyl, or they are united with each other to form a ring structure, R3 represents a protective group for phosphoric acid such as 2-cyanoethyl; and B1 represents an optionally substituted pyrimidine or purine base.

The present invention further relates to a method for the synthesis of a nucleoside represented by the general formula (I) by cyanoethyletherification of 2' hydroxyl group in the presence or absence of t-butylalcohol using as materials a compound selected from the group consisting of cesium carbonate, DBU and TritonB; acrylonitrile and a nucleoside derivative.

The present invention further relates to a phosphoramidite compound of the thus synthesized nucleoside. The phosphoramidite compound of the present invention may be easily prepared by those skilled in the art in accordance with the phosphoramidite method known to those skilled in the art. The present invention relates to a RNA oligomer comprising the above nucleoside excepting the moiety "X" and "Y" in the general formula (I).

Advantages of the Invention

According to the method of the present invention, it has become possible to efficiently perform cyanoethylation of various kinds of a hydroxyl group.

BEST MODE FOR CARRYING OUT THE INVENTION

Figure 1:
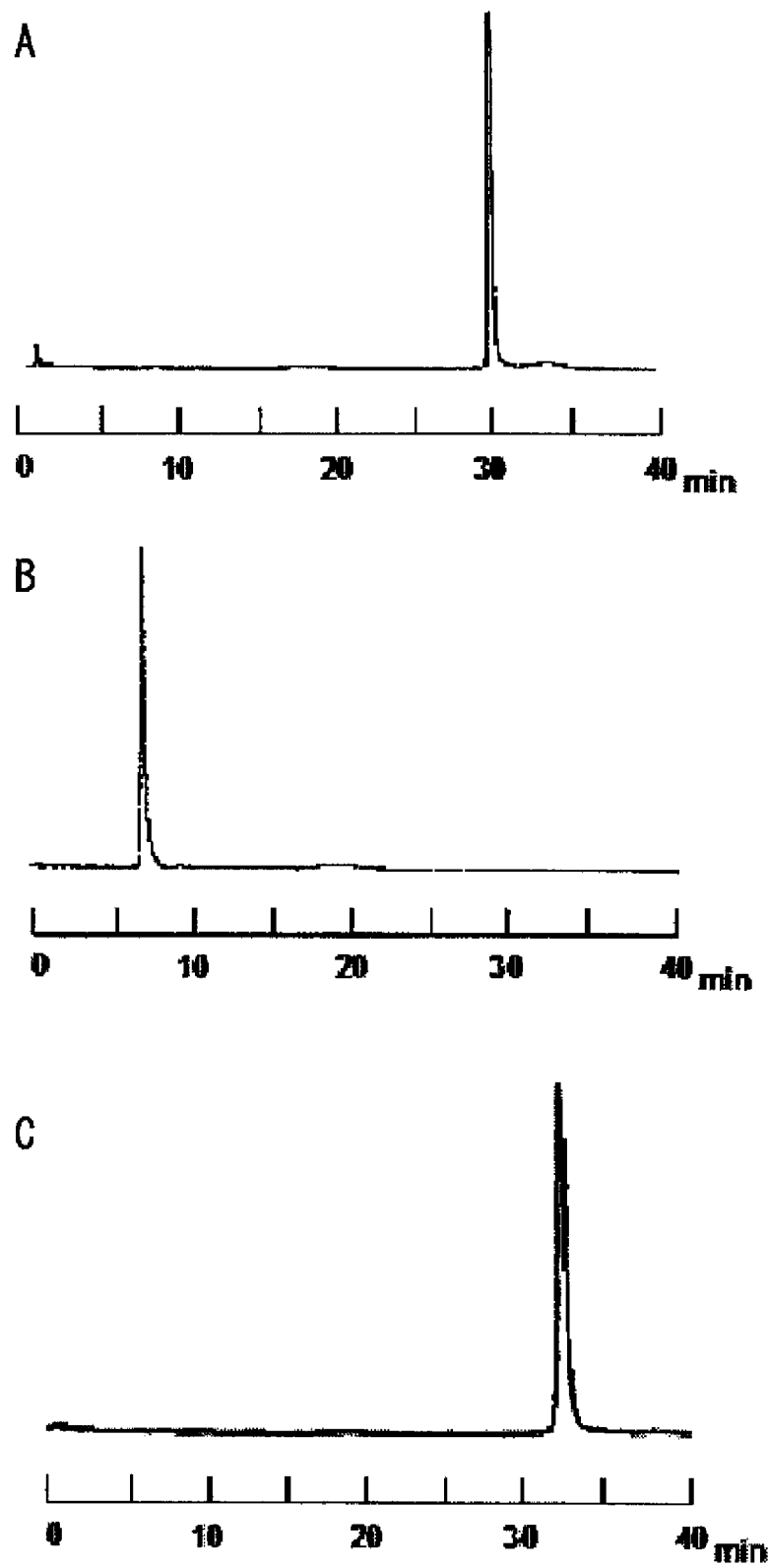
FIG. 1 shows a analysis profile obtained by anion exchange high performance liquid chromatography of the RNA oligomer obtained by the present invention.

Examples of the substituent of B1, the pyrimidine or purine base, are any one known for those skilled in the art, including those described in the examples of the present specification, such as N-dimethylaminomethylene, N-acetyl, triisopropylbenzenesulfonyl, etc. In the phosphoramidite group (II), R1 and R2 may be the same as or different from each other, representing an alkyl group having 1-7 carbon atoms such as diisopropyl, or they are united with each other to form a ring structure. The protective group for phosphoric acid, R3, includes 2-cyanoethyl, 4-nitrophenylethyl, N-(trifluoroacetyl)aminobutyl, or 4-[N-methyl-N-(2,2,2-trifluoroacetyl)amino]butyl, 2-cyanoethyl being preferred.

The method of the present invention uses the acrylonitrile and the nucleoside derivative in the presence of a compound selected from the group consisting of cesium carbonate, OBU and TritonB, preferably cesium carbonate. It is preferred to carry out the above method using said compound in a range of 0.1-30 equiv for the nucleoside derivative in the presence of t-butylalcohol in a range of 0.05-30 equiv for the acrylonitrile. The reaction is preferably carried out at a temperature of from 20° C. to 30° C. for 2-3 hours.

EXAMPLES

The present invention will be explained more in detail, which shall not limit the scope of the invention.

Example 1

2'-O-(2-cyanoethyl)-N-3-benzoyl-3',5'-O-tetraisopropyl disiloxanilidene uridine (Compound 1)

[Chemical formula 1]

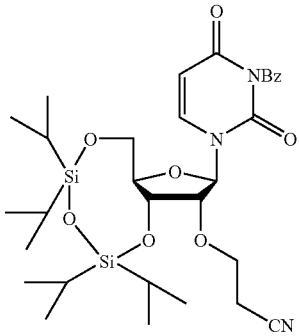

N3-benzoyl-3',5'-O-tetraisopropyl disiloxanilidene uridine compound (591 mg, 1 mmol) was dissolved in t-butylalcohol (5 ml). To this were added acrylonitrile (1.3 ml, 20 mmol) and then cesium carbonate (353 mg, 1 mmol), and vigorously stirred for 2 hours. Cesium carbonate was removed by filtration with celite, and the mixture was concentrated under a reduced pressure. The resulting residue was purified with silica gel column chromatography (hexane:ethyl acetate=3:1) to give a titled compound as white crystal (593 mg, 0.921 mmol) with a yield of 92%. The compound was crystallized from chloroform-diisopropylether and used as a sample for analysis.

m.p. 159° C.

$^1$H-NMR(CDCl$_3$, 500 MHz) 0.94-1.12(28H, m), 2.61-2.63 (2H, m), 3.91-4.05(4H, m), 4.18-4.29(3H, m), 5.70(1H, s), 5.79(1H, d, J=8.30), 7.49-7.94(5H, m), 8.00(1H, d, J=8.30)

Example 2

2'-O-(2-cyanoethyl)-N-3-benzoyluridine (Compound 2)

[Chemical formula 2]

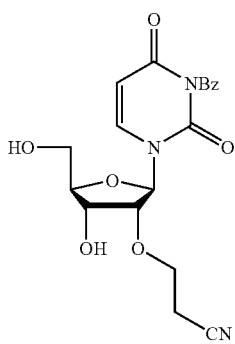

The resulting compound 1 (322 mg, 0.545 mmol) was dissolved in tetrahydrofuran (3 ml). Tetrahydrofuran solution (2 ml) of tetrabutylammonium fluoride (327 mg, 1.25 mmol) and acetic acid (72 μl, 1.25 mmol) was dropped slowly into the above solution. After being stirred for one hour, the reaction solution was diluted with chloroform and washed with saturated saline solution three times. After an organic layer was removed, an aqueous layer was extracted with chloroform. The resulting extract was combined with the organic layer, dried over anhydrous sodium sulfate, filtered and concentrated under reduced pressure. The resulting residue was purified with silica gel column chromatography (ethyl acetate:acetone=10:1) to give a titled compound as white foamy material (147 mg, 0.366 mmol) with a yield of 67%.

$^1$H-NMR(CDCl$_3$, 500 MHz) 2.63-2.66(2H, m), 3.83-3.90 (2H, m), 4.04-4.09(4H, m), 4.31(1H, dd, J=5.37, 7.32), 5.81 (1H, d, J=1.71), 5.83(1H, d, J=8.30), 7.50-7.94(5H, m), 8.10 (1H, d, J=8.30)

Example 3

2'-O-(2-cyanoethyl)-N-3-uridine (Compound 3)

[Chemical formula 3]

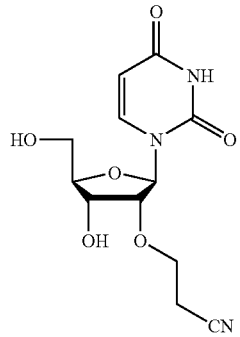

The resulting compound 2 (80 mg, 0.202 mmol) was dissolved in ethanol:ammonia solution (2 ml, 3:1 v/v) and stirred for 3 hours and concentrated under reduced pressure. The resulting residue was dissolved in methanol (1 ml), diluted with ether (10 ml) and extracted with distilled water (3 ml) three times. An aqueous layer was concentrated under reduced pressure and the resulting residue was purified with spherical silica gel column chromatography (chloroform:methanol=5:1) to give a titled compound as white foamy material (57 mg, 0.191 mmol) with a yield of 95%.

$^1$H-NMR(D$_2$O, 500 MHz) 2.70-2.72(2H, m), 3.69(1H, dd, J=4.15, 12.9 Hz), 3.82-3.85(3H, m), 4.02-4.04(1H, m), 4.08 (1H, dd, J=3.66, 5.23), 4.19(1H, t, J=5.62, 6.10), 5.77(1H, d, J=8.06), 5.87(1H, d, J=3.66), 7.80(1H, d, J=8.06)

Example 4

5'-O-(4,4'-dimethoxytrityl)-2'-O-(2-cyanoethyl)-N-3-benzoyl uridine (Compound 4)

[Chemical formula 4]

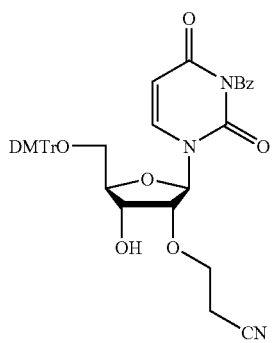

The compound 1 (2.70 g, 4.19 mmol) was dissolved in tetrahydrofuran (20 ml). Tetrahydrofuran solution (20 ml) of tetrabutylammonium fluoride (2.75 g, 10.5 mmol) and acetic acid (0.6 ml, 10.5 mmol) was dropped slowly into the above solution. After being stirred for seven hours, the reaction solution was diluted with chloroform and washed with saturated saline three times. The extract of an aqueous layer with chloroform was combined with an organic layer, dried over anhydrous sodium sulfate, filtered and concentrated under reduced pressure. The resulting residue was purified with silica gel column chromatography (ethyl acetate:acetone=10:1) to give the compound 2. The compound was then subjected to azeotropy for dehydration with dry pyridine three times and dissolved in dry pyridine (40 ml). To this was added dimethoxytrityl chloride (1.71 g, 5.04 mmol) and stirred for seven hours. The reaction was stopped by addition of water into the reaction system. The residue obtained by concentration under reduced pressure was diluted with chloroform and washed with saturated sodium bicarbonate solution and saturated saline solution. The resulting organic layer was dried over anhydrous sodium sulfate, filtered and concentrated under reduced pressure. The resulting residue was purified with silica gel column chromatography (hexane:ethyl acetate=1:1) to give a titled compound as white foamy material (2.07 g, 2.84 mmol) with a yield of 70%.

$^1$H-NMR(CDCl$_3$, 500 MHz) 2.55-2.62(3H, m), 3.57-3.64 (2H, m), 3.79-3.86(7H, m), 4.00(1H, d, J=5.13), 4.04-4.07 (1H, m), 4.12-4.15(1H, m), 4.53(1H, ddd, J=5.13, 9.40, 9.52), 5.37(1H, d, J=8.30), 5.86(1H, s), 6.86(4H, dd, J=1.22, 8.79), 7.24-7.34(7H, m), 7.42(2H, br), 7.49(2H, br), 7.64(2H, br), 7.93(2H, br), 8.22(1H, J=8.30)

Example 5

5'-O-(4,4-dimethoxytrityl)-2'-O-(2-cyanoethyl)-N-3-benzoyl uridine (2-cyanoethyl N,N-diisopropyl phosphoramidite) (Compound 5)

[Chemical formula 5]

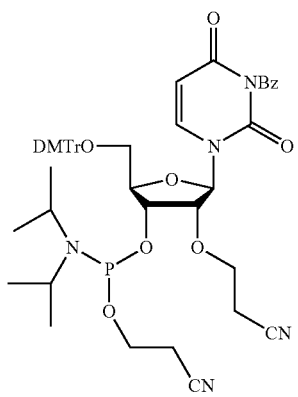

The compound 4 was dried in a desiccator with the use of diphosphorus pentoxide as desiccant under reduced argon atmosphere. The resulting dried compound 4 (1.06 g, 1.51 mmol) and tetrazolediisopropyl ammonium salt (193 mg, 2.25 mmol) were dissolved in dry acetonitrile (7 ml). To this was dropped a dryacetonitrile solution (3 ml) of 2-cyanoethyl N,N-diisopropyl phosphorodiamidite (678 mg, 2.25 mmol). After being stirred for 5 hours, the reaction solution was diluted with chloroform, washed with saturated saline solution two times and with saturated sodium bicarbonate solution two times. The extract of an aqueous layer with chloroform was combined with an organic layer, dried over anhydrous sodium sulfate, filtered and concentrated under reduced pressure. The resulting residue was purified with spherical silica gel column chromatography (hexane:ethylacetate=1:1, 0.5% triethylamine) to give a titled compound as white foamy material (1.27 g, 1.40 mmol) with a yield of 93%.

$^1$H-NMR(CDCl$_3$, 500 MHz) 1.08-1.30(12H, m), 2.47-2.68 (4H, m), 3.49-4.30(16H, m), 4.59-4.80(1H, br), 5.28-5.37 (1H, m), 5.85(1H, m), 6.83-6.91(4H, m), 7.24-7.66(13H, m), 8.00-8.03(2H, m), 8.24-8.30(1H, m)

Example 6

5'-O-(4,4'-dimethoxytrityl)-2'-O-(2-cyanoethyl)-uridine (Compound 6)

[Chemical formula 6]

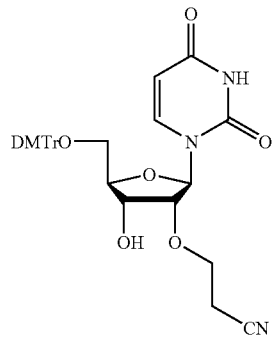

2'-O-cyanoethyluridine (Compound 3) (1.97 g, 6.63 mmol) was dissolved in pyridine (70 ml), mixed with dimethoxytritylchloride (2.47 g, 7.29 mmol) and stirred for 4 hours. The reaction solution was concentrated under reduced pressure, diluted with chloroform, and washed with saturated saline solution and saturated sodium bicarbonate solution. The resulting organic layer was dried over anhydrous sodium sulfate and concentrated under reduced pressure. The resulting residue was purified with silica gel column chromatography (chloroform:methanol, 100:0→20:1, 0.5% triethylamine) to give a titled compound (3.91 g) with a yield of 99%.

$^1$H-NMR (CDCl$_3$, 500 MHz) 2.68-2.71(2H, m), 3.53-3.58 (2H, m), 3.78-3.79(6H, m), 3.90-3.98(2H, m), 4.03-4.06(1H, m), 4.17-4.22(1H, m), 4.49(1H, dd), 5.31(1H, d), 5.89(1H, s), 6.84(4H, d), 7.22-7.40(9H, m), 8.06(1H, d)

Example 7

5'-O-(4,4'-dimethoxytrityl)-2'-O-(2-cyanoethyl)uridine 3'-(2-cyanoethyl N,N-diisopropyl phosphoramidite) (Compound 7)

[Chemical formula 7]

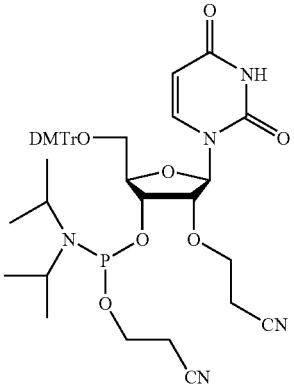

The compound 6 (1.20 g, 2.00 mmol) was subjected to azeotropy for dehydration with dry toluene five times, followed by argon-substitution. It was then dissolved in dry dichloromethane (10 ml). To this were added dropwise diisopropylethylamine (0.5 ml, 2.87 mmol) and a dry dichloromethane solution (2 ml) of 2-cyanoethyl-N,N-diisopropylaminochlorophosphine (521 mg, 2.20 mmol). After being stirred for two hours at a room temperature, the reaction solution was washed with saturated sodium bicarbonate solution twice and with saturated saline solution twice. The resulting organic layer was dried over anhydrous sodium bicarbonate solution, filtered and concentrated under reduced pressure. The resulting residue was purified with silica gel column chromatography (chloroform:methanol, 100:0→50:1) to give a titled compound (1.33 g) with a yield of 83%.

$^1$H-NMR(CDCl$_3$, 500 MHz) 1.08-1.21(12H, m), 2.60-2.77 (4H, m), 3.43-3.76(4H, m), 3.79-3.80(6H, m), 3.87-4.84(6H, m), 5.18-5.29(1H, m), 5.88-5.90(1H, m), 6.81-6.87(4H, m), 7.23-7.39(9H, m), 8.05-8.13(1H, m)

Example 8

N4-dimethylaminomethylene-3',5'-O-tetraisopropyl disiloxanilidene-2'-O-(2-cyanoethyl)cytidine (Compound 8)

[Chemical formula 8]

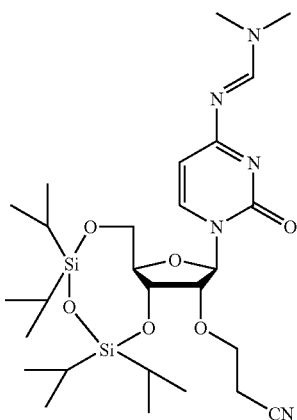

N4-dimethylaminomethylene-3',5'-O-tetraisopropyl disiloxanilidene cytidine (541 mg, 1 mmol) was dissolved in t-butylalcohol (5 ml). To this were added acrylonitrile (1.3 ml, 20 mmol) and then cesium carbonate (353 mg, 1 mmol), and vigorously stirred for 3 hours. Cesium carbonate was removed by filtration with celite, followed by concentration under reduced pressure. The resulting residue was purified with silica gel column chromatography (chloroform:methanol=40:1) to give a titled compound (538 mg) with a yield of 89%.

$^1$H-NMR (CDCl$_3$, 500 MHz) 0.85-1.06(28H, m), 2.69-2.73(2H, m), 3.10(3H, s), 3.12(3H, s), 3.86-4.24(7H, m), 5.74(1H, s), 6.01(1H, dd), 8.01(1H, d), 8.76(1H, s)

Example 9

N4-dimethylaminomethylene-2'-O-(2-cyanoethyl) cytidine (Compound 9)

[Chemical formula 9]

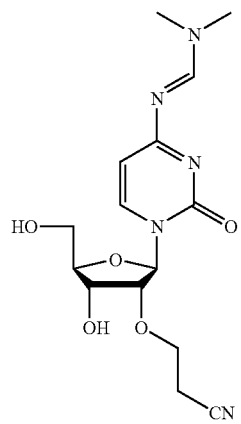

The compound 8 (347 mg, 0.584 mmol) was dissolved in tetrahydrofuran (6 ml). To this were added triethylamine hydrogen trifluoride (332 µl, 2.04 mmol) and then triethylamine (147 µl, 1.05 mmol) and stirred for one hour. The reaction solution was concentrated under reduced pressure and the resulting residue was purified with silica gel column chromatography (chloroform:methanol=100:0→50:1) to give a titled compound (184 mg) with a yield of 90%.

$^1$H-NMR(CDCl$_3$, 500 MHz) 0.85-1.06(28H, m), 2.69-2.73 (2H, m), 3.10(3H, s), 3.12(3H, s), 3.86-4.24 (7H, m), 5.74 (1H, vs), 6.01(1H, dd), 8.01(1H, d), 8.76 (1H, s)

Example 10

N4-dimethylaminomethylene-5'-O-dimethoxytrityl-2'-O-cyanoethylcytidine (Compound 10)

[Chemical formula 10]

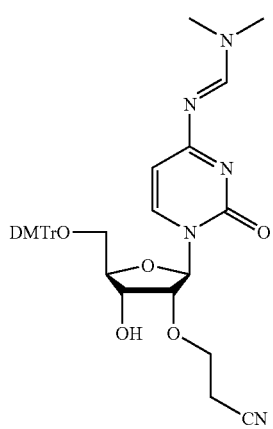

The compound 9 (192 mg, 0.546 mmol) was dissolved in pyridine (5 ml) mixed with dimethoxytritylchloride (204 mg, 0.602 mmol) and stirred for 2 hours. The reaction solution was concentrated under reduced pressure, diluted with chloroform, and washed with saturated saline solution and saturated sodium bicarbonate solution. The extract obtained from an aqueous layer by the reverse extraction with chloroform three times was combined with an organic layer, dried over anhydrous sodium sulfate, filtered and concentrated under reduced pressure. The resulting residue was purified with silica gel column chromatography (chloroform:methanol, 100:0→25:1) to give a titled compound (157 mg) with a yield of 45%.

¹H-NMR(CDCl₃, 500 MHz) 2.69-2.73(2H, br), 3.10(3H, s), 3.12(3H, s), 3.49(1H, dd), 3.57-3.59(1H, m), 3.77(6H, s), 3.94-4.07(3H, m), 4.31-4.41(2H, m), 5.76(1H, d), 5.93(1H, s), 6.82-6.85(4H, m), 7.20-7.43(9H, m), 8.16(1H, dd), 8.76 (1H, s)

Example 11

2'-O-(2-cyanoethyl) cytidine (Compound 11)

[Chemical formula 11]

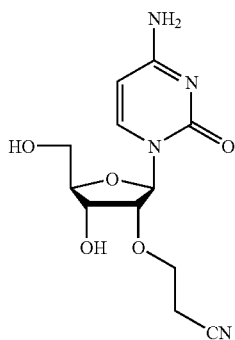

The compound 10 (351 mg, 0.4 mmol) was dissolved in conc. ammonia water-ethanol (3:1, v/v, 4 ml) and stirred for one hour. The reaction solution was concentrated under reduced pressure and purified with silica gel column chromatography (chloroform:methanol=70:1) to give a titled compound (109 mg) with a yield of 92%.

¹H-NMR(D₂O, 500 MHz) 2.83-2.86(2H, m), 3.84(1H, dd, J=13 Hz, 4.4 Hz), 3.95-4.03(3H, m) 4.14-4.18(2H, m), 4.27 (1H, dd, J=13 Hz, 1.7 Hz), 5.97(1H, d, J=3.2 Hz), 6.1(1H, d, J=7.6 Hz), 7.89 (1H, d, J=7.6 Hz).

Example 12

N4-acetyl-2'-O-(2-cyanoethyl) cytidine (Compound 12)

[Chemical formula 12]

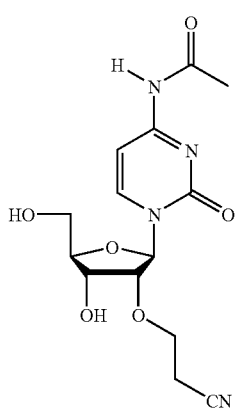

The compound 11 (1000 mg, 3.38 mmol) was dissolved in ethanol (70 ml), mixed with anhydrous acetic acid (1.6 ml, 16.96 mmol) and stirred for 12 hours. The precipitated crystal was filtered out and washed with diethylether to give a titled compound (1055 mg, 3.12 mmol) with a yield of 92%.

¹H-NMR (DMSO, 500 MHz) 2.10 (3H, s), 2.81-2.86 (2H, m), 3.60-3.63 (1H, m), 3.78-3.94 (5H, m), 4.03-4.05 (1H, m), 5.13 (1H, d, J=4.88), 5.20 (1H, t, J=4.88), 5.78 (1H, d, J=1.71), 7.18(d, J=7.57), 8.47(1H, J=7.57), 10.92(1H, s)

Example 13

N4-acetyl-5'-O-dimethoxytrityl-2'-O-(2-cyanoethyl) cytidine (Compound 13)

[Chemical formula 13]

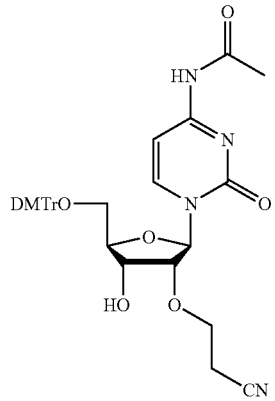

The compound 12 (1055 mg, 3.12 mmol) was subjected to azeotropy for dehydration with dry pyridine four times and dissolved in dry pyridine (30 ml). Dimethoxytritylchloride (1162 mg, 3.43 mmol) was added to the solution. After being stirred for three hours, the reaction was stopped by addition of water. The reaction solution was concentrated under reduced pressure, diluted with chloroform, and washed with saturated saline solution and saturated sodium bicarbonate solution. The resulting organic layer was dried over anhydrous sodium sulfate, filtered and concentrated under reduced pressure. The resulting residue was purified with silica gel column chromatography (chloroform:methanol, 98:2, 0.5% triethylamine) to give a titled compound as white foamy material (1848 mg, 2.88 mmol) with a yield of 92%.

¹H-NMR (CDCl₃, 500 MHz) 2.20 (3H, s), 2.60-2.68 (2H, m), 2.97-2.98 (1H, br), 3.54-3.62 (2H, m), 3.79 (6H, m), 3.92-3.97 (1H, m), 4.01(1H, d, J=5.13), 4.11-4.13(1H, m), 4.24-4.18(1H, m), 5.89 (1 H, s), 6.85-6.87 (4 H, m), 7.15-7.43 (10 H, m), 8.53 (1H, s), J=7.57), 10.00 (1H, br)

Example 14

N4-acetyl-5'-O-dimethoxytrityl-2'-O-(2-cyanoethyl) cytidine 3'-(2-cyanoethyl N,N-diisopropylphosphoramidite) (Compound 14)

[Chemical formula 14]

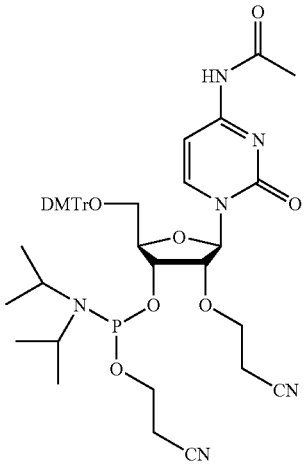

The compound 13 (668 mg, 1.04 mmol) was subjected to azeotropy for dehydration with dry toluene five times, followed by argon-substitution. It was then dissolved in dry dichloromethane (8 ml). To this were added diisopropylethylamine (271 μl, 1.56 mmol) and a dry dichloromethane solution (2 ml) of diisopropylamino-(2-cyanoethyl)-chlorophosphine (271 mg, 1.15 mmol). After being stirred for three hours, the reaction solution was diluted with ethyl acetate, and washed with saturated sodium bicarbonate solution twice and with saturated saline solution twice. The resulting organic layer was dried over anhydrous sodium bicarbonate solution and filtered. Solvent was then distilled out under reduced pressure. The resulting residue was purified with silica gel column chromatography (chloroform:methanol, 98:2→97:3, 0.5% triethylamine) to give a titled compound as white foamy material (790 mg, 0.94 mmol) with a yield of 90%.

$^1$H-NMR (CDCl$_3$, 500 MHz) 1.01-1.18 (12 H, m), 2.23-2.24(3 H, m), 2.40-2.75(4 H, m), 3.45-3.74(5H, m), 3.81-3.82(6 H, m), 3.84-4.59(6 H, m), 5.91-5.93(1 H, m), 6.83-6.87(4 H, m), 6.96-7.05(1H, m), 7.26-7.44(9H, m), 8.53-8.60 (1H, m), 10.10(1H, s)

Example 15

N6-dimethylaminomethylene-3,5'-O-tetraisopropyl disiloxanilidene-2'-O-cyanoethyl adenosine (Compound 15)

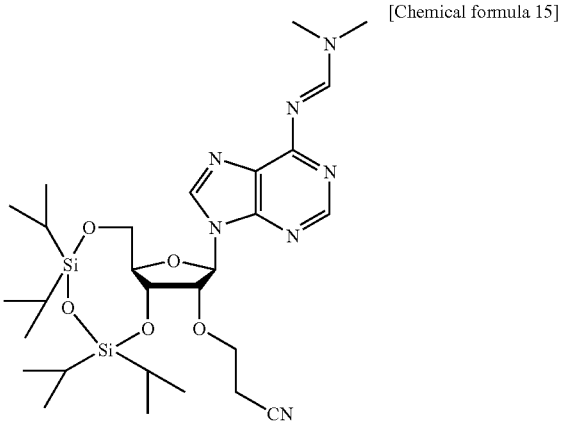

[Chemical formula 15]

N6-dimethylaminomethylene-3',5'-O-tetraisopropyl disiloxanilidene adenosine (565 mg, 1 mmol) was dissolved in t-butylalcohol (5 ml). To this were added acrylonitrile (1.3 ml, 20 mmol) and then cesium carbonate (353 mg, 1 mmol), and vigorously stirred for 3 hours. Cesium carbonate was removed by filtration with celite, followed by concentration under reduced pressure. The resulting residue was purified with silica gel column chromatography (chloroform:methanol=50:1) to give a titled compound (559 mg) with a yield of 90%.

$^1$H-NMR(CDCl$_3$, 500 MHz) 0.96-1.12(28H, m), 2.71-2.73 (2H, m), 3.19(3H, s), 3.25(3H, s), 3.94-4.27(6H, m), 4.77 (1H, dd), 6.01(1H, s), 8.14(1H, s), 8.48(1H, s), 8.93(1H, s)

Example 16

N6-dimethylaminomethylene-2'-O-cyanoethyladenosine (Compound 16)

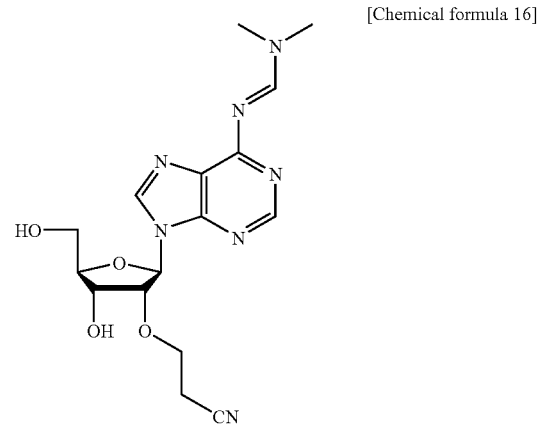

[Chemical formula 16]

The compound 15 (1.45 g, 2.35 mmol) was dissolved in tetrahydrofuran (24 ml). To this were added triethylamine hydrogen trifluoride (1.3 ml, 7.98 mmol) and then triethylamine (589 μl, 4.23 mmol) and stirred for one hour. The reaction solution was concentrated under reduced pressure and the resulting residue was purified with silica gel column chromatography (chloroform:methanol=50:1→25:1) to give a titled compound (878 mg, quant).

$^1$H-NMR(CD$_3$OD, 500 MHz) 2.62-2.65(2H, m), 3.16(3H, s), 3.18(3H, s), 3.65-3.72(4H, m), 3.80-3.86(4H, m), 4.09-4.11(1H, m), 4.43(1H, t), 4.53(1H, t), 6.08(1H, d), 8.34(1H, s), 8.40(1H, s), 8.83(1H, s)

Example 17

N6-dimethylaminomethylene-5'-O-dimethoxytrityl-2-O-cyanoethyl adenosine (Compound 17)

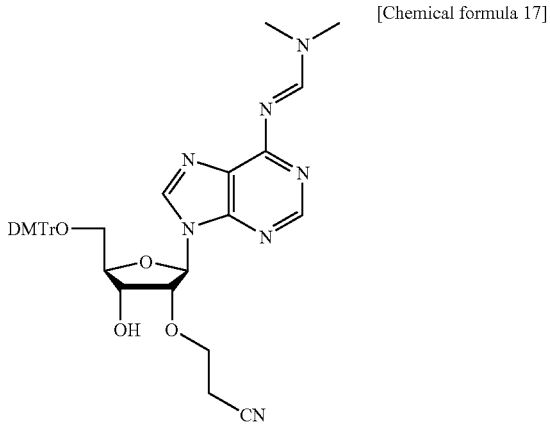

[Chemical formula 17]

The compound 16 (716 mg, 1.91 mmol) was dissolved in pyridine (19 ml), mixed with dimethoxytritylchloride (712 mg, 2.10 mmol) and stirred for 3 hours. The reaction solution was concentrated under reduced pressure, diluted with chloroform, and washed with saturated saline solution and saturated sodium bicarbonate solution. The extract obtained from an aqueous layer by the reverse extraction with chloroform three times was combined with an organic layer, dried over anhydrous sodium sulfate, filtered and concentrated under reduced pressure. The resulting residue was purified with silica gel column chromatography (chloroform:methanol, 100:0→50:1, 0.5% triethylamine) to give a titled compound (1132 mg) with a yield of 87%.

$^1$H-NMR(CDCl$_3$, 500 MHz) 2.52-2,2.59 (2H, m), 3.13 (3H, s), 3.18(3H, s), 3.25-3.57(2H, m), 3.72(6H, s), 3.82-3.92 (2H, m), 4.20-4.24(3H, m), 4.50(1H, t), 4.60(1H, dd) 6.14 (1H, d), 6.75(4H, d), 7.13-7.47(9H, m), 8.09 (1H, s), 8.43(1H, s), 8.94(1H, s)

Example 18

N6-dimethylaminomethylene-5'-O-dimethoxytrityl-2'-O-(2-cyanoethyl) adenosine 3'-(2-cyanoethyl N,N-diisopropylphosphoramidite) (Compound 18)

[Chemical formula 18]

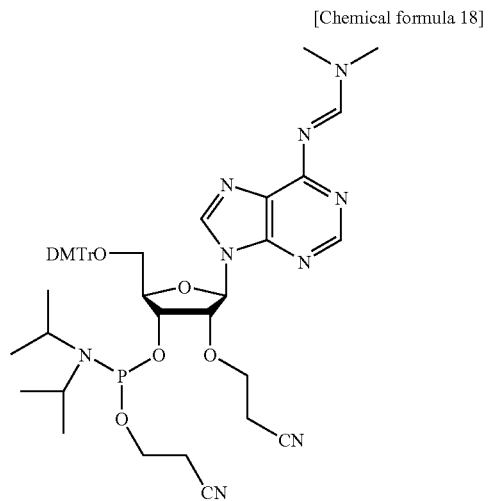

The compound 17 (1.06 g, 1.51 mmol) was subjected to azeotropy for dehydration with dry toluene five times, followed by argon-substitution. It was then dissolved in dry dichloromethane (12 ml). To this were added dropwise diisopropylethylamine (0.3 ml, 1.72 mmol) and a dry dichloromethane solution (2 ml) of 2-cyanoethyl N,N-diisopropylamino chlorophosphine (328 mg, 1.36 mmol). After being stirred for 2 hours at a room temperature, the reaction solution was diluted with chloroform, and washed with saturated sodium bicarbonate solution three times and with saturated saline solution once. The resulting organic layer was dried over anhydrous sodium bicarbonate solution, filtered and concentrated under reduced pressure. The resulting residue was purified with NH silica gel column chromatography (chloroform:methanol, 100:0→100:1) to give a titled compound (896 mg) with a yield of 82%.

$^1$H-NMR (CDCl$_3$, 500 MHz) 1.06-1.18(12H, m), 2.58-2.66(4H, m), 3.21(3H, s), 3.26(3H, s), 3.32-3.35(1H, m), 3.51-4.01(14H, m), 4.34-4.39(1H, m), 4.55-4.67(1H, m), 4.80-4.85(1H, m), 6.10-6.14(1H, m), 6.76-6.83(4H, t), 7.18-7.36(9H, m), 8.09-8.12(1H, m), 8.45-8.46(1H, m), 8.95-8.96 (1H, m)

Example 19

N2-dimethylaminomethylene-O-6-triisopropylbenzenesulfonyl-3',5'-O-tetraisopropyldisiloxanilidene-2'-O-cyanoethyl guanosine (Compound 19)

[Chemical formula 19]

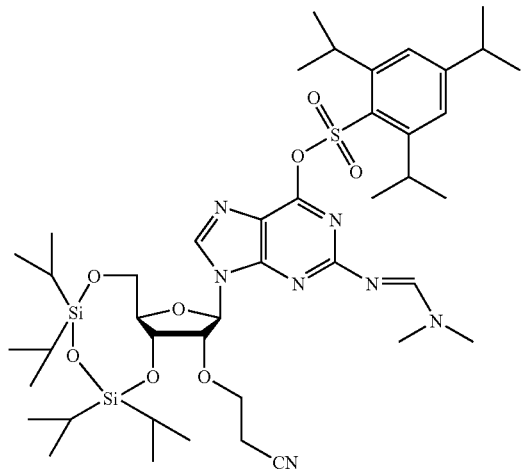

N2-dimethylaminomethylene-O-6-triisopropylbenzenesulfonyl-3',5'-O-tetraisopropyldisiloxanilidene guanosine (6.60 g, 80 mmol) was dissolved in t-butylalcohol (39 ml). To this were added acrylonitrile (20 ml, 156 mmol) and then cesium carbonate (2.75 g, 7.80 mmol), and vigorously stirred for 2 hours. Cesium carbonate was removed by filtration with celite, followed by concentration under reduced pressure. The resulting residue was purified with silica gel column chromatography (chloroform:methanol=100:1) to give a titled compound (5.82 mg) with a yield of 83%.

$^1$H-NMR(CDCl$_3$, 500 MHz) 0.99-1.34(46H, m), 2.77-2.632.79(2H, t), 2.95-2.97(1H, m), 3.11 (3H, s), 3.16(3H, s), 3.99-4.33(9H, m), 4.57(1H, dd), 6.18(1H, s), 7.23(2H, s), 8.04(1H, s), 8.23(1H, s)

Example 20

N2-dimethylaminomethylene-6-O-triisopropylbenzenesulfonyl-2'-O-cyanoethyl guanosine (Compound 20)

[Chemical formula 20]

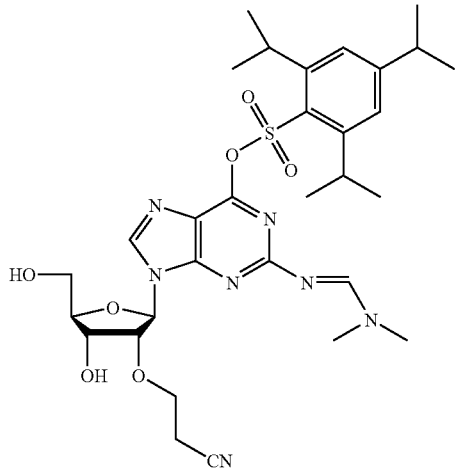

The compound 19 (113 mg, 0.126 mmol) was dissolved in tetrahydrofuran (1 ml). To this were added triethylamine hydrogen trifluoride (72 μl, 0.442 mmol) and then triethylamine (31 μl, 0.226 mmol) and stirred for one hour. The reaction solution was concentrated under reduced pressure and the resulting residue was purified with silica gel column chromatography (chloroform:methanol=100:0→50:1→10:1) to give a titled compound (67 mg) with a yield of 81%.

$^1$H-NMR(CDCl$_3$, 500 MHz) 1.22-1.31(18H, m), 2.57-2.60 (2H, t), 2.81-2.96(1H, m), 3.05(3H, s), 3.12(3H, s), 3.62-3.79 (3H, m), 3.93(1H, d), 4.24(2H, dt), 4.31(1H, br), 4.62(1H, m), 4.84(1H, dd), 5.98-6.15(2H, m), 7.23(2H, s), 8.12(1H, s), 8.20(1H, s)

Example 21

N2-dimethylaminomethylene-2'-O-cyanoethylguanosine (Compound 21)

[Chemical formula 21]

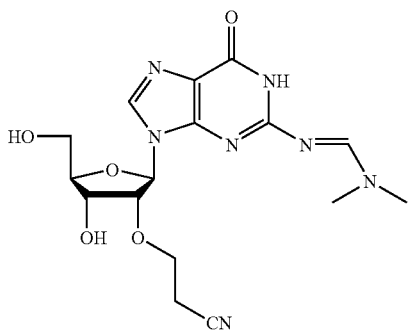

The compound 13 (630 mg, 0.7 mmol) was dissolved in anhydrous acetonitrile (7 ml). To this were added orthonitrobenzaldoxime (349 mg, 2.10 mmol) and tetramethylguanidine (263 μl, 2.10 mmol). After being stirred for one hour, the reaction solution was diluted with ethyl acetate, and washed with saturated saline solution and saturated ammonium chloride. The resulting organic layer was dried over anhydrous sodium bicarbonate solution, filtered and subjected to distillation under reduced pressure. The resulting residue was dissolved in anhydrous THF (7 ml) and mixed with triethylamine (172 μl, 1.26 mmol) and triethylamine hydrogen trifluoride (399 ml, 2.45 mmol) and stirred for one hour.

The resulting residue was then purified with silica gel column chromatography (chloroform:methanol, 90:10→85:15, v/v) to give a titled compound as white solid (215 mg, 0.557 mmol) with a yield of 80%.

$^1$H-NMR (DMSO, 500 MHz) 2.73-2.76 (2H, m), 3.03 (3H, s), 3.15 (3H, s), 3.54-3.58 (1H, m), 3.63-3.69 (1H, m), 3.78-3.82 (1H, m), 3.91 (1H, q, J=3.91), 4.29 (1H, q, J=4.39, 5.13), 4.40 (1H, t, J=5.13), 5.01 (1H, t, J=5.61), 5.30 (1H, d, J=5.37), 5.91 (1H, d, J=5.13), 8.08 (1H, s), 8.55 (1H, s), 11.4 (1H, br)

Example 22

2'-O-cyanoethyl cytidine

[Chemical formula 22]

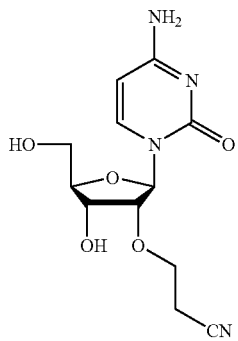

The compound 12 (141 mg, 0.401 mmol) was dissolved in ammonia water:ethanol (4 ml, v/v=3/1) and stirred for one hour. The reaction solution was then concentrated under rediced pressure, and the residue was then purified with silica gel column chromatography (chloroform:methanol, 7:1) to give a titled compound (109 mg) with a yield of 92%.

$^1$H-NMR(D$_2$O, 500 MHz) 2.83-2.86(2H, m), 3.83(1H, dd), 3.95-4.03(3H, m), 4.14-4.18(2H, m) r 4.28(1H, dd), 5.97 (1H, d) 6.05(1H, dd), 7.88(1H, d)

Example 23

2'-cyanoethyl adenosine

[Chemical formula 23]

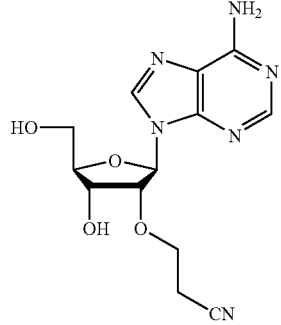

The compound 16 (475 mg, 1.27 mmol) was dissolved in acetonitrile. To this was added hydrazine (218 μl, 7 mmol) and stirred for three hours. Powder precipitated in the reaction system was washed with isopropylalcohol. The resulting filtrate was concentrated under reduced pressure and the resulting residue was then purified with silica gel column chromatography (chloroform:methanol, 100:0→50:1→10:1). The thus purified compound was combined with said powder to give a titled compound (332 mg) with a yield of 82%.

$^1$H-NMR (D$_2$O, 500 MHz) 2.83-2.86(2H, m), 3.83(1H, dd), 3.95-4.03(3H, m), 4.14-4.18(2H, m), 4.28(1H, dd), 5.97 (1H, d), 6.05(1H, dd), 7.88(1H, d)

Example 24

2'-cyanoethyl guanosine

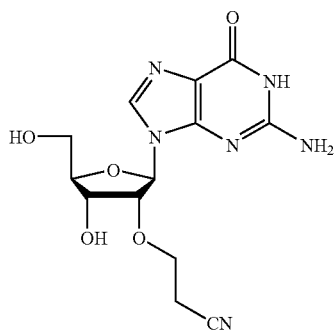

The compound 21 (447 mg, 0.680 mmol) was dissolved in anhydrous acetonitrile (7 ml). To this were added orthonitrobenzaldoxime (339 mg, 7 mmol) and tetramethylguanidine (85 μl, 0.677 mmol). After being stirred for one hour, the reaction solution was concentrated under reduced pressure and the resulting residue was then purified with silica gel column chromatography (chloroform:methanol, 100:0→50:1→20:1→10:1, v/v). The resulting compound was mixed with ammonia water:ethanol (5 ml, v/v=3:1) and stirred for six hours. The reaction solution was concentrated under reduced pressure and subjected to crystallization to give a titled compound (121 mg) with a yield of 53%.

$^1$H-NMR (D$_2$O, 500 MHz) 2.73(2H, t), 3.76-3.95(4H, m), 4.23(1H, q), 4.50(1H, dd), 4.52(1H, t), 5.98(1H, d), 8.04(1H, s)

Example 25

2N-dimethylaminomethylene-5'-O-dimethoxytrityl-2'-O-(2-cyanoethyl)guanosine (Compound 25)

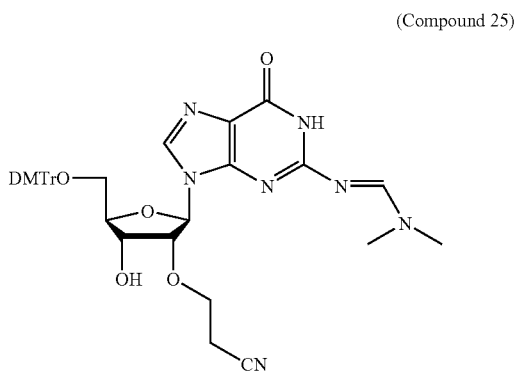

The compound 21 (392 mg, 1.00 mmol) was subjected to azeotropy for dehydration with dry pyridine four times and dissolved in dry pyridine (10 ml). Dimethoxytritylchloride (373 mg, 1.10 mmol) was added to the solution. After stirring for three hours at a room temperature, the reaction was stopped by addition of water. The solvent was distilled out under reduced pressure. The resulting residue was diluted with chloroform, and washed with saturated saline solution and saturated sodium bicarbonate solution. An organic layer was dried over anhydrous sodium sulfate, and the solvent was distilled out under reduced pressure. The resulting residue was purified with silica gel column chromatography (chloroform:methanol, 98:2, 0.5% triethylamine) to give a titled compound as white foamy material (635 mg, 0.92 mmol) with a yield of 92%.

$^1$H-NMR (CDCl$_3$, 500 MHz) 2.57-2.59 (2 H, m), 2.98(3 H, s), 3.04(3 H, s), 3.38(1 H, dd, J=4.64. 10.50), 3.45-3.47(1 H, dd, J=2.44, 10.50), 3.74(6 H, s), 3.78-3.96(3 H, m), 4.21-4.23(1 H, m), 4.29(1 H, dd, J=3.42, 8.55), 4.59-4.60(1H, m), 6.09(1H, dd, J=3.42), 6.10-6.78(4H, m), 7.13-7.41(9H, m), 7.74 (1H, s), 8.54(1H, s), 10.01(1H, br)

Example 26

2N-dimethylaminomethylene-5'-O-dimethoxytrityl-2'-O-(2-cyanoethyl) guanosine 3'-(2-cyanoethyl N,N-diisopropylphosphoramidite) (Compound 26)

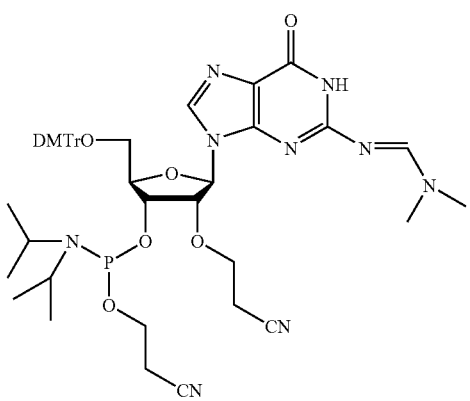

The compound 25 (1.95 g, 2.81 mmol) was subjected to azeotropy for dehydration with dry toluene three times and, followed by argon-substitution, which was then dissolved in dry dichloromethane (26 ml). To this were added diisopropylethylamine (736 μl, 1.56 mmol) and a dry dichloromethane solution (2 ml) of diisopropylamino-(2-cyanoethyl)-chlorophosphine (732 mg, 3.09 ml). After being stirred for three hours, the reaction solution was diluted with chloroform, and washed with saturated sodium bicarbonate solution twice and with saturated saline solution twice. The resulting organic layer was dried over anhydrous sodium bicarbonate solution and filtered. Solvent was then distilled out under reduced pressure. The resulting residue was purified with silica gel column chromatography (chloroform:methanol, 98:2, 0.5% triethylamine) to give a titled compound as white foamy material (2.11 g, 2.36 mmol) with a yield of 84%.

$^1$H-NMR (CDCl$_3$, 500 MHz) 1.01-1.24(12 H, m), 2.33-2.66(5 H, m), 3.07-3.10(6 H, m), 3.30-4.02(14 H, m), 4.29-4.35(2 H, m), 4.48-4.55(1 H, m), 6.09-6.12(1 H, m), 6.79-6.82(4H, m), 7.17-7.44(10 H, m), 7.78-7.82(1H, m), 8.57-8.60(1H, m), 9.73-9.77(1H, m)

Example 27

Synthesis of 12-mer of 2'-cyanoethyluridylic acid

RNA synthesis program (condensation time: 10 min.) was carried out using anhydrous acetonitrile solution of 2'-O-cyanoethyluridine phosphoramidite unit (compound 7, 0.1M) by means of a DNA/RNA automatic synthesizer (Applied Bio System) provided with a long aminoalkyl chain CPG (1 μl) in which 2'-O-cyanoethyluridine was introduced via a succinyl linker by a conventional way (16 μl mol/g), which was filled into a socket for solid-phase synthesis. After the synthesis had been completed, the resulting oligonucleotide was excised from the solid phase by treatment with ammonia water (1 ml) for 20 min. After diluted appropriately with ammonium acetate buffer, the oligonucleotide was purified with a reverse phase column cartridge and an anion exchange HPLC. The oligonucleotide obtained by a desalting operation with the reverse phase column cartridge was lyophilized to give a titled compound with a yield of 21%. Analysis profile obtained in the anion exchange HPLC is shown in FIG. 1A.

MALDI TOF MASS (negative) Calcd. 4245.66 Found 4244.33

Example 28

Synthesis of 2'-cyanoethyl RNA tetra-mer having Mixed Sequence "GACU"

RNA synthesis program (condensation time: 10 min.) was carried out using four kinds of anhydrous acetonitrile solution of 2'-O-cyanoethyluridine phosphoramidite unit (compounds 7, 14, 18 and 26, 0.1M) by means of a DNA/RNA automatic synthesizer (Applied Bio System) provided with a long aminoalkyl chain CPG (1 μl) in which 2'-O-cyanoethyluridine was introduced via a succinyl linker by a conventional way (16 μl mol/g), which was filled into a socket for solid-phase synthesis. After the synthesis had been completed, excision of the resulting oligonucleotide from the solid phase and removal of a protecting group of the nucleic acid base moiety were carried out by treatment with ammonia water-ammonium acetate (10% wt/wt: 1 ml) for 90 min. After diluted appropriately with ammonium acetate buffer, the oligonucleotides were purified with a reverse phase column cartridge and an anion exchange HPLC. The oligonucleotides obtained by a desalting operation with the reverse phase column cartridge were lyophilized to give a titled compound with a yield of 58%. Analysis profile obtained in the anion exchange HPLC is shown in FIG. 1B.

MALDI TOF MASS (negative) Calcd. 1434.31 Found 1434.12

Example 29

Synthesis of 2'-cyanoethyl RNA 12-mer having Mixed Sequence "GACUGACUGACU"

RNA synthesis program (condensation time: 10 min.) was carried out using four kinds of anhydrous acetonitrile solution of 2'-O-cyanoethyluridine phosphoramidite unit (compounds 7, 14, 18 and 26, 0.1M) by means of a DNA/RNA automatic synthesizer (Applied Bio System) provided with a long aminoalkyl chain CPG (1 μl) in which 2'-O-cyanoethyluridine was introduced via a succinyl linker by a conventional way (16 μl mol/g), which was filled into a socket for solid-phase synthesis. After the synthesis had been completed, excision of the resulting oligonucleotide from the solid phase and removal of a protecting group of the nucleic acid base moiety were carried out by treatment with ammonia water-ammonium acetate (10% wt/wt: 1 ml) for 90 min. After diluted appropriately with ammonium acetate buffer, the oligonucleotides were purified with a reverse phase column cartridge or an anion exchange HPLC. The oligonucleotides obtained by a desalting operation with the reverse phase column cartridge were lyophilized to give a titled compound with a yield of 6%. Analysis profile obtained in the anion exchange HPLC is shown in FIG. 1C.

MALDI-TOF MASS (negative) Calcd. 4428.86 Found 4428.55

A modified RNA, a nucleoside that may be obtained according to the present method and is represented by the general formula (I), or a nucleotide derived therefrom, is useful as an artificial RNA molecule for gene regulation, etc:

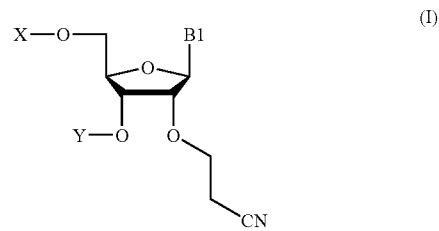

(I)

wherein X and Y may be the same as or different from each other, and are hydrogen, optionally substituted silyl group, 4-methoxytrityl group, 4,4'-dimethoxytrityl group or a group represented by the general formula (II):

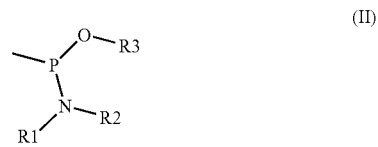

(II)

wherein R1 and R2 may be the same as or different from each other, representing an alkyl group having carbon atoms of 1-7 such as diisopropyl, or they are united with each other to form a ring structure, R3 represents a protective group for a phosphoric acid such as 2-cyanoethyl; and B1 represents an optionally substituted pyrimidine or purine base.

What is claimed is:

1. A nucleoside that is represented by the general formula (I) or a nucleotide derived therefrom:

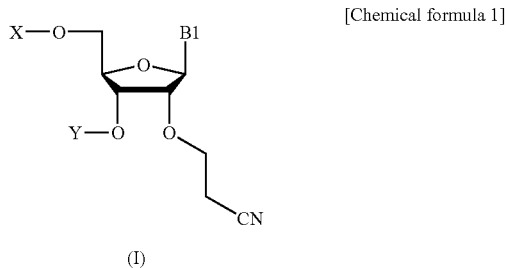

[Chemical formula 1]

(I)

wherein X and Y may be the same as or different from each other, and are hydrogen, optionally substituted silyl group, 4-methoxytrityl group, 4,4'-dimethoxytrityl group or a group represented by the general formula (II):

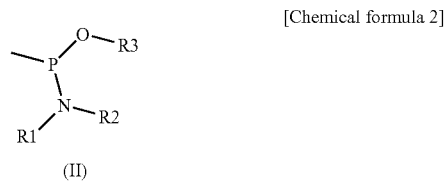

[Chemical formula 2]

(II)

wherein R1 and R2 may be the same as or different from each other, representing an alkyl group having 1-7 carbon atoms such as diisopropyl, or they are united with each other to form a ring structure, R3 represents a protective group for a phosphoric acid such as 2-cyanoethyl; and B1 represents an optionally substituted pyrimidine or purine base.

2. 2'-O-cyanoethyluridine.

3. 2'-O-cyanoethylcytidine.

4. 2'-O-cyanoethyladenosine.

5. 2'-O-cyanoethylguanosine.

6. N-4-dimethylaminomethylene-2'-O-cyanoethylcytidine.

7. N6-dimethylaminomethylene-2'-O-cyanoethyladenosine.

8. N2-dimethylaminomethylene-6-O-triisopropylbenzenesulfonyl-2'-O-cyanoethylguanosine.

9. N4-acetyl-2'-O-(2-cyanoethyl)cytidine.

10. N2-dimethylaminomethylene-2'-O-cyanoethylguanosine.

11. A method for the synthesis of a nucleoside according to any one of claims 1-10, which is characterized by cyanoethyletherification of 2' hydroxyl group in the presence or absence of t-butylalcohol using as materials a compound selected from the group consisting of cesium carbonate, DBU and TritonB; acrylonitrile and a nucleoside derivative.

12. A method according to claim 11 which is carried out using the compound selected from the group consisting of cesium carbonate, DBU and TritonB that is present in a range of 0.1-30 equiv for the nucleoside derivative in the presence of t-butylalcohol in a range of 0.05-30 equiv for the acrylonitrile.

13. A method according to claim 11 using cesiumcarbonate.

14. A method according to claim 11 which is carried out at a temperature of from 20° C. to 30° C.

15. A method according to claim 11 which is carried out for 2-3 hours.

16. A RNA oligomer comprising the nucleoside according to any one of claims 1-10.

* * * * *